(12) United States Patent
Al-Zaydia et al.

(10) Patent No.: US 10,358,425 B1
(45) Date of Patent: Jul. 23, 2019

(54) DIHYDROPYRIMIDONES AND PHARMACEUTICAL COMPOSITIONS THEREOF

(71) Applicant: King Abdulaziz University, Jeddah (SA)

(72) Inventors: Khadijah M. Al-Zaydia, Jeddah (SA); Norah Faihan Alqahtani, Jeddah (SA); Modi Al-Boqamia, Jeddah (SA); Mohamed H. Elnagdi, Cairo (EG)

(73) Assignee: King Abdulaziz Universkty, Jeddah (SA)

( * ) Notice: Subject to any disclaimer, the term of this patent is extended or adjusted under 35 U.S.C. 154(b) by 0 days.

(21) Appl. No.: 16/120,490

(22) Filed: Sep. 4, 2018

(51) Int. Cl.
| | | |
|---|---|---|
| *C07D 239/22* | (2006.01) | |
| *A61K 47/44* | (2017.01) | |
| *A61K 47/14* | (2017.01) | |
| *A61K 47/12* | (2006.01) | |

(52) U.S. Cl.
CPC ............ *C07D 239/22* (2013.01); *A61K 47/12* (2013.01); *A61K 47/14* (2013.01); *A61K 47/44* (2013.01)

(58) Field of Classification Search
CPC .............................. C07D 239/22; A61K 47/44
See application file for complete search history.

(56) References Cited

U.S. PATENT DOCUMENTS

| | | | | |
|---|---|---|---|---|
| 9,119,856 B1 * | 9/2015 | Al-Dhfyan | ............ | A61K 31/513 |
| 9,856,232 B1 * | 1/2018 | Bhat | ..................... | C07D 401/02 |
| 10,047,071 B1 * | 8/2018 | Bhat | ..................... | C07D 403/10 |
| 2009/0163545 A1 | 6/2009 | Goldfarb | | |

OTHER PUBLICATIONS

Gein, et al. ; New facilities of Biginelli reaction. Synthesis of methyl 6-aryl-5-benzoyl-4-methoxy-2- oxohexahydropyrimidine-4-carboxylates ; Russian Journal of Organic Chemistry ; vol. 53, Issue 11, pp. 1675-1677 ; Dec. 23, 2017 ; Abstract.
De Vita, et al. ; Discovery of in vitro antitubercular agents through in silico ligand-based approaches ; ScienceDirect ; European Journal of Medicinal Chemistry ; vol. 121, pp. 169-180 ; Oct. 2016 ; Abstract.
Tortorella, et al ; An Effective Virtual Screening Protocol to Identify Promising p53-MDM2 Inhibitors ; Journal of Chemical Information and Modeling ; pp. 1216-1227 ; 2016 ; Abstract.
Azizi, et al. ; Eutectic Salt Catalyzed Environmentally Benign and Highly Efficient Biginelli Reaction ; The Scientific World Journal, vol. 2012, Article 908702 ; Nov. 21, 2011 ; Abstract.
Ajala, et al. ; CoMFA and CoMSIA studies on fluorinated hexahydropyrimidine derivatives ; ScienceDirect ; Bioorganic & Medicinal Chemistry Letters, vol. 21, Issue 24 ; pp. 7392-7398 ; Dec. 15, 2011 ; Abstract.

Agbaje, et al. ; Synthesis and in vitro cytotoxicity evaluation of some fluorinated hexahydropyrimidine derivatives ; ScienceDirect ; Bioorganic & Medicinal Chemistry Letters, vol. 21, Issue 3 ; pp. 989-992 ; Feb. 1, 2011 ; Abstract.
Reactions of 6-aryl-5-benzoyl-4- dichloromethyl-4-hydroxyhexahydropyrimidin- 2-ones with hydrazine hydrate: A new simple and efficient route to 4-aryl-5-phenyl-3,4-dihydropyrimido[4,5-d]pyridazin-2(1 H)-ones ; Russian Chemical Bulletin, vol. 58, Issue 9 pp. 1981-1985 ; Sep. 2009 ; Abstract.
Ryabukhin, et al. ; Acyl pyruvates as synthons in the Biginelli reaction ; Tetrahedron Letters, vol. 51, Issue 32, pp. 4229-4232 ; Aug. 11, 2010 ; ABstract.
Brogi, et al. ; Pharmacophore Modeling for Qualitative Prediction of Antiestrogenic Activity ; Journal of Chemical Information and Modeling, 49 (11), pp. 2489-2498 ; 2009 ; Abstract.
Heterocyclization of functionalized heterocumulenes with C,N-, C,O-, and C,S-binucleophiles: X. 1-Chloroalkyl isocyanates in the synthesis of new 5-aroyldihydropyrimidines ; Russian Journal of Organic Chemistry, vol. 45 Issue 5, pp. 755-761 ; Jun. 9, 2009 ; Abstract.
Yang, et al. ; 5-Benzoyl-4-hydroxy-6-(4-nitrophenyl)-4-trifluoromethyl-3,4,5,6-tetrahydropyrimidin-2(1 H)-one monohydrate ; Organic Compunds ; Acta Crystal E65 PP87-88 ; 2009 ; Abstract.
Sacmaci, et al. ; New β-Tricarbonyl Compounds: Synthesis, Reactions with Urea and Some Thioureas ; The Japan Institute of Heterocyclic Chemistry Publication ; Regular Issue, vol. 75, No. 8, pp. 2013-2021 ; 2008 ; Apr. 1, 2008.
Ryabukhin, et al. ; CF -substituted 1,3-dicarbonyl compounds in the Biginelli reaction promoted by chlorotrimethylsilane ; Science Direct ; Journal of Fluorine Chemistry, vol. 129, Issue 7, pp. 625-631 ; Jul. 2008 ; Absract.
Khunt, et al. ; Green chemistry approach to synthesis of some new trifluoromethyl containing tetrahydropyrimidines under solvent free conditions ; Department of Chemistry, Saurashtra University ; ARKIVOC pp. 277-284 ; 2008 ; 8 Pages.
Dichloroacetylaroylmethanes as two-carbon synthons in the Biginelli reaction ; Chemistry of Heterocyclic Compunds, vol. 42, Issue 9, pp. 1229-1232 ; Sep. 2006 ; Abstract.
Saripinar, et al. ; A Convenient Synthesis of Functionalized 1 H-Pyrimidine-2-ones/thiones, Pyridazine and Imidazole; Experimental Data and PM3 Calculations; The Japan Institute of Heterocyclic Chemistry Publication ; Regular Issue, vol. 68, No. 10, pp. 2045-2061 ; Aug. 25, 2006 ; Abstract.
One-step solvent-free synthesis of fluoroalkyl-substituted 4-hydroxy-2-oxo (thioxo)hexahydropyrimidines in the presence of 1-butyl-3-methylimidazolium tetrafluoroborate ; Russian Journal of Organic Chemistry, vol. 42, Issue 9, pp. 1392-1395 ; Sep. 2006 ; Abstract.
Shanmugam, et al. ; Regioselective dehydrogenation of 3,4-dihydropyrimidin-2 (1H)-ones mediated by ceric ammonium nitrate ; ScienceDirectl Tetrahedron, vol. 62, Issue 41, pp. 9726-9734 ; Oct. 9, 2006 ; Abstract.
Fluorocontaining 1,3-Dicarbonyl Compounds in the Synthesis of Pyrimidine Derivatives ; Russian Journal of Organic Chemistry, vol. 37, Issue 6, pp. 869-880 ; Jun. 2001 ; Abstract.

(Continued)

*Primary Examiner* — Golam M Shameem (74) *Attorney, Agent, or Firm* — Oblon, McClelland, Maier & Neustadt, L.L.P.

(57) ABSTRACT

A series of heterocyclic compounds containing a dihydropyrimidone or dihydropyrimidinthione functionality. Pharmaceutical compositions containing the compounds and methods of producing the compounds via ultrasonication are also provided.

11 Claims, 3 Drawing Sheets

(56) References Cited

OTHER PUBLICATIONS

Ma, et al . ; Lanthanide Triflate Catalyzed Biginelli Reaction. One-Pot Synthesis of Dihydropyrimidinones under Solvent-Free Conditions ; The Journal of Organic Chemistry, 65 (12), pp. 3864-3868 ; May 18, 2000 ; Abstract.
Saloutin, et al. ; Biginelli condensations of fluorinated 3-oxo esters and 1,3-diketones ; ScienceDirect; Journal of Fluorine Chemistry, vol. 103, Issue 1, pp. 17-23 ; Apr. 3, 2000 ; Abstract.
Hugel ; Microwave Multicomponent Synthesis ; Molecules, 14, pp. 4936-4972 ; 2009 ; 37 Pages.
Wan, et al. ; Chemo-/regioselectric synthesis of 6-unsubstituted dihydropyrimidinones, 1,3-thiazines and chromones via novel variants of Biginelli reaction ; Chemical Communications, Issu 19 ; 2009 ; Abstract.
Savant, et al. ; Synthesis of some novel trifluoromethylated tetrahydropyrimidines using etidronic acid and evaluation for antimicrobial activity; Scholars Research Library ; 2018 ; Abstract.
Chaudhari ; Synthesis and biological evaluation of (4-(trifluoromethyl)-hexahydro-4-hydroxy-1-methyl-6-aryl-2-thioxopyrimidin-5-yl)(4-methoxyphenyl)methanone derivatives ; Ogranic Chemsitry, vol. 8, Issue 8 ; Feb. 21, 2012 ; 6 pages.
Zhu, et al. ; Microwave-Assisted Synthesis of New Spiro[indoline-3,4'-quinoline] Derivatives via a One-Pot Multicomponent Reaction ; Synthetic Communications ; An International Journal for Rapid COmmunication of Synthetic Organic Chemistry, vol. 39 ; 2009 ; Abstract.

\* cited by examiner

DIHYDROPYRIMIDONES AND PHARMACEUTICAL COMPOSITIONS THEREOF

BACKGROUND OF THE INVENTION

Technical Field

The present invention relates to a family of heterocyclic compounds having a dihydropyrimidone or dihydropyrimidinthione moiety. A pharmaceutical composition containing the heterocyclic compounds and a method of preparing the compounds are disclosed.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Figure 1:
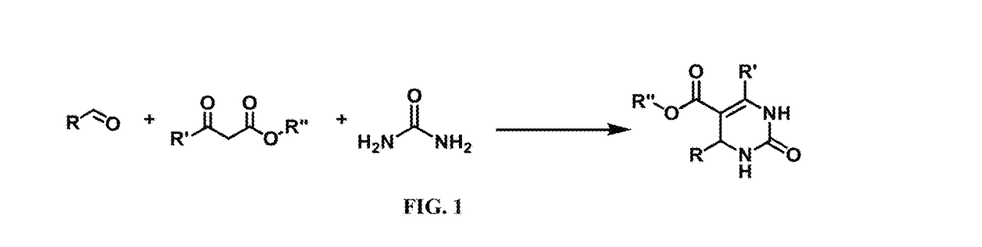
FIG. 1 is a reaction scheme for a three-component Biginelli reaction of a β-ketoester, an aldehyde and urea.
Figure 2:
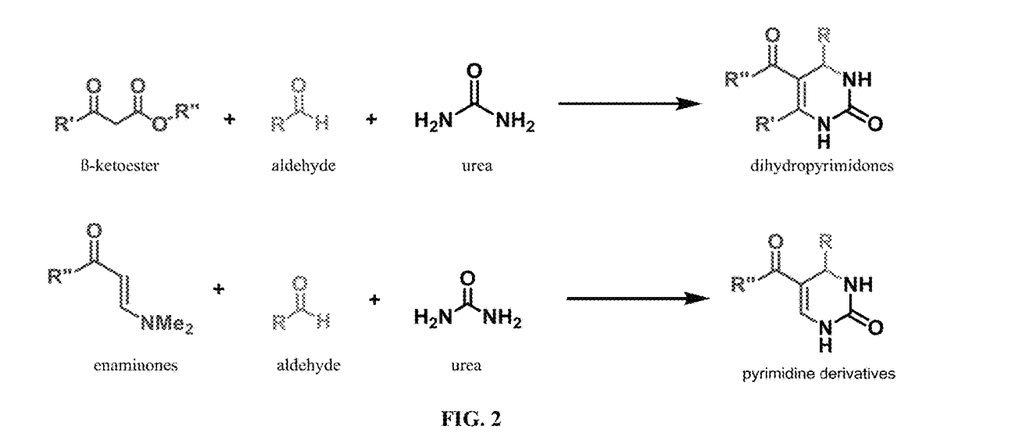
FIG. 2 is a comparison between Biginelli reaction starting from a β-ketoester, an aldehyde and urea and a variation of Biginelli reaction starting from an enaminone, an aldehyde and urea.

In the year 1891, Pietro Biginelli reported a one-pot reaction producing a new class of heterocyclic compounds which are known now as Biginelli adducts in his honor [P. Biginelli. Intorno ad uramidi aldeidiche dell'etere acetilacetico, Gazz Chim Ital, 21 (1891), pp. 455-461; P. Biginelli. Intorno ad uramidi aldeidiche dell'etere acetilacetico. II, Gazz Chim Ital, 21 (1891), pp. 497-500; P. Biginelli. Ueber Aldehyduramide des Acetessigathers, Ber Dtsch Chem Ges, 24 (1891), pp. 1317-1319; P. Biginelli. Ueber Aldehyduramide des Acetessigathers. II, Ber Dtsch Chem Ges, 24 (1891), pp. 2962-2967; and P. Biginelli. Aldehyde-urea derivatives of aceto- and oxaloacetic acids, Gazz Chim Ital, 23 (1893), pp. 360-413]. The one-pot three-component reaction of urea, an aromatic aldehyde and a β-ketoester which yields a dihydropyrimidine is known as the Biginelli reaction (FIG. 1) [Wang, Z. Comprehensive Organic Names Reactions and Reagents, 3V Set, Wiley: 2009]. The unsustainability of traditional methods of performing chemical syntheses has led to a rise in multicomponent reactions that combine multiple starting materials with various functional groups. Because of their high efficiency and small environmental impact, Biginelli reactions that yield complex target molecules have gained substantial interest [Bussolari, C., J; McDonnell, A., P. A New Substrate for the Biginelli Cyclocondensation: Direct Preparation of 5-Unsubstituted 3,4-Dihydropyrimidin-2(1H)-ones from a β-Keto Carboxylic Acid. J. Org. Chem., 2000, 65 (20), 6777-6779; and Wan, J.; Pan, Y. Chemo-/regioselective synthesis of 6-unsubstituted dihydropyrimidinones, 1,3-thiazines and chromones via novel variants of Biginelli reaction. Chem. Commun., 2009, 2768-2770, each incorporated herein by reference in their entirety]. Modern variations of Biginelli reaction include replacing the β-ketoester with an enaminone (FIG. 2) [Zhu, S. L.; Zhao, K.; Su, X. M.; Ji, S. J. Microwave-assisted synthesis of new spiro[indoline-3,4'-quinoline] derivatives via a one-pot multicomonent reaction. Synth. Commun. 2009, 39, 1355-1366; and Helmut M. Hugel. Microwave Multicomponent Synthesis. Molecules 2009, 14(12), 4936-4972, each incorporated herein by reference in their entirety].

In recent years, ultrasound has been implemented in chemical reactions, which has evolved into the field of sonochemistry. The equipment needed for ultrasonication is relatively inexpensive, and the use of ultrasound as a method of chemical activation has many applications [James H. Clark, Duncan Macquarrie. Handbook of Green Chemistry and Technology, 16, 376-383, Wiley: 2002; and T. J. Mason and J.-L. Luche, Ultrasound as a new tool for synthetic chemists, Chemistry under Extreme or Non-classical Conditions, ed. R. van Eldick and C. D. Hubbard, John Wiley, New York, 1997, pp. 317]. Stefani et al. reported a simple and efficient protocol for conducting Biginelli reactions using ultrasound. Several novel dihydropyrimidones were prepared through the Biginelli reaction promoted by ultrasound irradiation [Stefani, H. A.; Oliveira, C. B.; Almeida, R. B.; Pereira, C. M. P.; Braga, R. C.; Cella, R.; Borges, V. C.; Savegnago, L.; Nogueira, C. W. Dihydropyrimidin-(2H)-ones obtained by ultrasound irradiation: a new class of potential antioxidant agents, Eur J Med Chem, 41 (4) (2006), pp. 513-518, incorporated herein by reference in its entirety]. Other researchers also suggested that ultrasound irradiation could accelerate a classic Biginelli reaction [Zhidovinova, M. S., Fedorova, O. V., Rusinov, G. L. et al. Sonochemical synthesis of Biginelli compounds, Russian Chemical Bulletin, 2003, 52, pp. 2527-2528; and Yonghong Zhang, Bin Wang, Xiaomei Zhang, Jianbin Huang, Chenjiang Liu. An Efficient Synthesis of 3,4-Dihydropyrimidin-2 (1H)-Ones and Thiones Catalyzed by a Novel Bronsted Acidic Ionic Liquid under Solvent-Free Conditions. Molecules, 2015, 20, pp. 3811-3820, each incorporated herein by reference in their entirety]. Despite availability of several dihydropyrimidone-based drugs in market, there is still a need to synthesize new dihydropyrimidones for medicinal use.

In view of the forgoing, one objective of the present disclosure is to provide dihydropyrimidone and dihydropyrimidinthione compounds prepared via Biginelli reaction under ultrasonication. Another objective of the present disclosure is to provide pharmaceutical compositions comprising the compounds, and methods of preparing the compounds.

BRIEF SUMMARY OF THE INVENTION

According to a first aspect, the current disclosure relates to a compound of formula (I)

or a salt thereof, a solvate thereof, a tautomer thereof, a stereoisomer thereof, or a mixture thereof, wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, and a halogen, (ii) each $R_2$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, a halogen, a nitro, and a cyano, (iii) $R_3$ is selected from the group consisting of a hydrogen, an optionally substituted alkyl, an optionally substituted cycloalkyl, and an optionally substituted arylalkyl, (iv) $R_4$ is selected from the group consisting of a hydrogen, an optionally substituted alkyl, an optionally substituted cycloalkyl, and an optionally substituted arylalkyl, and (v) X is O or S.

In one embodiment, each $R_1$ is a hydrogen.
In one embodiment, each $R_2$ is a hydrogen.
In one embodiment, $R_3$ is a hydrogen.
In one embodiment, $R_4$ is a hydrogen.
In one embodiment, X is O.
In one embodiment, the compound of formula (I) of the first aspect is According to a second aspect, the current disclosure relates to a pharmaceutical composition, comprising the compound of formula (I) of the first aspect and a pharmaceutically acceptable carrier and/or excipient.

In one embodiment, the pharmaceutically acceptable carrier and/or excipient is at least one selected from the group consisting of a buffer, an inorganic salt, a fatty acid, a vegetable oil, a synthetic fatty ester, a surfactant, and a polymer.

In one embodiment, the pharmaceutical composition comprises up to 10% by weight of the pharmaceutically acceptable carrier and/or excipient relative to a total weight of the pharmaceutical composition.

In one embodiment, the compound is or a salt thereof, a solvate thereof, or a mixture thereof.

According to a third aspect, the current disclosure relates to a method of synthesizing the compound of formula (I) of the first aspect in which X is O. The method involves mixing an enaminone of formula (II)

or a salt, solvate, tautomer or stereoisomer thereof, with an aldehyde of formula (III)

or a salt, solvate, or stereoisomer thereof, and a urea of formula (IV)

or a salt, solvate, tautomer or stereoisomer thereof in the presence of an acid and a solvent to form a mixture, and subjecting the mixture to ultrasound irradiation thereby forming the compound, wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, and a halogen, (ii) each $R_2$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, a halogen, a nitro, and a cyano, (iii) $R_3$ is selected from the group consisting of a hydrogen, an optionally substituted alkyl, an optionally substituted cycloalkyl, and an optionally substituted arylalkyl, (iv) $R_4$ is selected from the group consisting of a hydrogen, an optionally substituted alkyl, an optionally substituted cycloalkyl, and an optionally substituted arylalkyl, and (v) $R_x$ and $R_y$ are each independently an optionally substituted alkyl.

In one embodiment, the mixture is subjected to ultrasound irradiation at a temperature of 40-90° C.

In one embodiment, the mixture is subjected to ultrasound irradiation for 0.1-12 hours.

In one embodiment, the mixture is subjected to ultrasound irradiation at a frequency of 10-200 kHz.

In one embodiment, a molar ratio of the enaminone of formula (II) to the aldehyde of formula (III) is in the range of 1:2 to 2:1.

In one embodiment, a molar ratio of the aldehyde of formula (III) to the urea of formula (IV) is in the range of 1:2 to 2:1.

In one embodiment, the acid is present at a concentration of 1-40 mM relative to a total volume of the mixture.

In one embodiment, the acid is acetic acid.

In one embodiment, the solvent is ethanol.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Embodiments of the present disclosure will now be described more fully hereinafter with reference to the accompanying drawings, in which some, but not all embodiments of the disclosure are shown.

The present disclosure will be better understood with reference to the following definitions. Unless otherwise specified, "a" or "an" means "one or more". Within the description of this disclosure, where a numerical limit or range is stated, the endpoints are included unless stated otherwise. Also, all values and subranges within a numerical limit or range are specifically included as if explicitly written out.

As used herein, the terms "compound" and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The present disclosure is further intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{15}N$, isotopes of oxygen include $^{17}O$ and $^{18}O$, and isotopes of sulfur include $^{33}S$, $^{34}S$ and $^{36}S$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

As used herein, the term "alkyl" unless otherwise specified refers to both branched and straight chain saturated aliphatic primary, secondary, and/or tertiary hydrocarbon fragments of typically $C_1$ to $C_{20}$. Non-limiting examples of such hydrocarbon fragments include methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl. As used herein, the term optionally includes substituted alkyl groups. Exemplary moieties with which the alkyl group can be substituted may be selected from the group including, but not limited to, hydroxy, amino, alkylamino, arylamino, alkoxy, aryloxy, nitro, cyano, sulfonic acid, sulfate, phosphonic acid, phosphate, halo, or phosphonate or mixtures thereof. The substituted moiety may be either protected or unprotected as necessary, and as known to those skilled in the art.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

As used herein, the term "aryl" unless otherwise specified refers to functional groups or substituents derived from an aromatic ring including, but not limited to, phenyl, biphenyl, napthyl, thienyl, and indolyl. As used herein, the term optionally includes both substituted and unsubstituted moieties. Exemplary moieties with which the aryl group can be substituted may be selected from the group including, but not limited to, hydroxy, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The term "halogen", as used herein, means fluoro, chloro, bromo and iodo.

According to a first aspect, the current disclosure relates to a compound of formula (I)

(I)

or a salt thereof, a solvate thereof, a tautomer thereof, a stereoisomer thereof, or a mixture thereof.

Each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, and a halogen. In one or more embodiments, each $R_1$ is independently selected from the group consisting of a hydrogen, a methyl, a methoxy, a hydroxy, and a chloro. In a preferred embodiment, each $R_1$ is a hydrogen.

Each $R_2$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, a halogen, a nitro, and a cyano. In one or more embodiments, each $R_2$ is independently selected from the group consisting of a hydrogen, a methyl, a methoxy, a hydroxy, a chloro, a bromo, and a nitro. In a preferred embodiment, each $R_2$ is a hydrogen.

$R_3$ is selected from the group consisting of a hydrogen, an optionally substituted alkyl, an optionally substituted cycloalkyl, and an optionally substituted arylalkyl. In one or more embodiments, $R_3$ is selected from the group consisting of a hydrogen, a methyl, an ethyl, a n-propyl, an isopropyl, a tent-butyl, a sec-butyl, a hydroxymethyl, and a hydroxyethyl. In a preferred embodiment, $R_3$ is a hydrogen.

$R_4$ is selected from the group consisting of a hydrogen, an optionally substituted alkyl, an optionally substituted cycloalkyl, and an optionally substituted arylalkyl. In one or more embodiments, $R_4$ is selected from the group consisting of a hydrogen, a methyl, an ethyl, a n-propyl, an isopropyl, a tert-butyl, a sec-butyl, a hydroxymethyl, and a hydroxyethyl. In a preferred embodiment, $R_4$ is a hydrogen.

The element X may be O or S. In a preferred embodiment, X is O.

In one or more embodiments, the compound of formula (I) is

The present disclosure is further intended to include a compound of formula (IA)

or a salt thereof, a solvate thereof, a tautomer thereof, a stereoisomer thereof, or a mixture thereof, wherein:

$R_a$ can be an optionally substituted aryl, or an optionally substituted heteroaryl, and $R_b$ can be an optionally substituted alkyl, an optionally substituted aryl, or an optionally substituted heteroaryl. Exemplary aryls include phenyl, biphenyl, naphthyl, anthracenyl, and the like. The term "heteroaryl" refers to an aryl group where at least one aromatic ring contains one or more heteroatoms (e.g. nitrogen, oxygen, sulfur). Non-limiting examples of heteroaryl include, but are not limited to, furyl, thienyl, pyrrolyl, imidazolyl, pyrazolyl, triazolyl, tetrazolyl, pyridyl (or its N-oxide), pyrimidinyl (or its N-oxide), isoquinolyl (or its N-oxide), quinolyl (or its N-oxide), pyrazinyl, triazinyl, indolyl, 1H-indolyl, oxazolyl, isoxazolyl, thiazolyl, and isothiazolyl.

According to a second aspect, the current disclosure relates to a pharmaceutical composition, comprising the compound of formula (I) of the first aspect and a pharmaceutically acceptable carrier and/or excipient.

In one or more embodiments, the compound is or a salt thereof, a solvate thereof, or a mixture thereof.

As used herein, a "composition" or a "pharmaceutical composition" refers to a mixture of the active ingredient with other chemical components, such as pharmaceutically acceptable carriers and excipients. One purpose of a composition is to facilitate administration of the compound disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the compound represented by formula (I), a salt thereof, a solvate thereof, a tautomer thereof, a stereoisomer thereof, or any mixtures thereof. In some embodiments, other active ingredients in addition to the compound of the current disclosure may be incorporated into a pharmaceutical composition.

In one or more embodiments, the pharmaceutical composition comprises up to 0.01%, 0.1%, 1%, 5%, or 10% by weight of the pharmaceutically acceptable carrier and/or excipient relative to a total weight of the pharmaceutical composition. In one or more embodiments, the pharmaceutical composition comprises at least 0.01 wt %, 0.05 wt %, 0.1 wt %, 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt % of the compound of formula (I) relative to the total weight of the pharmaceutical composition. In some embodiments, the composition comprises up to 0.1 wt %, 1 wt %, 5 wt %, or 10 wt % of a pharmaceutically acceptable salt of the compound of formula (I). In some embodiments, the composition comprises up to 0.1 wt %, 1 wt %, 5 wt %, or 10 wt % of a pharmaceutically acceptable solvate of the compound of formula (I). Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

Many Biginelli adducts have active biological profiles, providing their potential as novel therapeutics for use in both humans and animals [De Fatima, A.; Braga, T. C.; Neto, L. S.; Terra, B. S.; Oliveira, B. G. F.; da Silva, D. L.; Modolo, L. V. A mini-review on Biginelli adducts with notable pharmacological properties. J. Adv. Res. 2015, 6, pp. 363-373, incorporated herein by reference in its entirety]. In addition, a number of 1,4-dihydropyridines are used as human drugs, especially for treating hypertension. Other commonly used dihydropyridine based drugs include amlodipine, lercanidipine, nimodipine, benidipine, azelnipidine, manidipine, etc. [Velena, A.; Zarkovic, N.; Troselj, K. G.; Bisenieks, E.; Krauze, A.; Poikans, J.; Duburs, G. 1,4-Dihydropyradine Derivatives: Dihydronicotinamide Analogues—Model Compounds Targeting Oxidative Stress. Oxidative Medicine and Cellular Longevity, 2016, 35 pages, incorporated herein by reference in its entirety]. Certain 1,4-dihydropyridine derivatives have been investigated for their potential as stabilizers for animal feed. As intermediates in the synthesis of compounds such as alkaloids, ibogaine, and discorine, 1,2-dihydropyridines are also of interest. The well-known drug Tamiflu may also be synthesized from a 1,2-dihydropyridine compound [Sharma, V. K.; and Singh, S. K. Synthesis, utility and medicinal importance of 1,2- and 1,4-dihydropyridines. RSC Adv. 2017, 7, pp. 2682-2732, incorporated herein by reference in its entirety].

In some embodiments, the active ingredient of the current disclosure, e.g. the compound represented by formula (I), a salt thereof, a solvate thereof, a tautomer thereof, a stereoisomer thereof, or any mixtures thereof, is expected to find utility as an anticancer agent in reducing the viability of cancer cells derived from human cancer cell lines including, but not limited to, colon cancer cell lines (e.g. HT-29), lung cancer cell lines (e.g. NCI-H460), breast cancer cell lines (e.g. MCF-7, and SK-BR-3), brain tumor cell lines (e.g. U251), ovarian cancer cell lines (e.g. NCI-ADR/RES, OVCAR-03), colon cancer cell lines (e.g. HT29), prostate cancer cell lines (e.g. PC-3), renal cancer cell lines (e.g. 786-0), and melanoma cell lines (e.g. UACC-62).

In some embodiments, the active ingredient of the current disclosure is also useful as a calcium channel inhibitor for the treatment of diseases and conditions including cardiovascular diseases (e.g. hypertension, coronary artery disease, angina, and arrhythmia), an anti-inflammatory agent, an antimicrobial agent, and/or an antioxidant for scavenging reactive oxygen species (ROS) and reactive nitrogen species (RNS).

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the pharmaceutical composition having the compound of formula (I), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to a third aspect, the current disclosure relates to a method of synthesizing the compound of formula (I) of the first aspect in which X is O. The method involves mixing an enaminone of formula (II)

(II)

or a salt, solvate, tautomer or stereoisomer thereof, with an aldehyde of formula (III)

(III)

or a salt, solvate, or stereoisomer thereof, and a urea of formula (IV)

(IV)

or a salt, solvate, tautomer or stereoisomer thereof in the presence of an acid and a solvent to form a mixture, and subjecting the mixture to ultrasound irradiation thereby forming the compound, wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, and a halogen, (ii) each $R_2$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, a halogen, a nitro, and a cyano, (iii) $R_3$ is selected from the group consisting of a hydrogen, an optionally substituted alkyl, an optionally substituted cycloalkyl, and an optionally substituted arylalkyl, (iv) $R_4$ is selected from the group consisting of a hydrogen, an optionally substituted alkyl, an optionally substituted cycloalkyl, and an optionally substituted arylalkyl, and (v) $R_x$ and $R_y$ are each independently an optionally substituted alkyl.

In a preferred embodiment, reacting the enaminone with the aldehyde and the urea in the presence of an acid to form the compound of formula (I) is performed in a polar solvent, preferably in ethanol (EtOH). Exemplary additional polar solvents that may be used in addition to, or in lieu of ethanol include, but are not limited to, methanol, n-butanol, isopropanol, n-propanol, tetrahydrofuran, ethyl acetate, acetone, acetonitrile, dimethyl sulfoxide, nitromethane and propylene carbonate, or mixtures thereof. It is equally envisaged that the reaction may be adapted to be performed in a non-polar solvent (i.e. pentane, cyclopentane, hexane, cyclohexane, benzene, toluene, 1,4-dioxane, chloroform, diethyl ether, dichloromethane, and mixtures thereof). In certain embodiments, reacting the enaminone with the aldehyde and the urea in the presence of an acid is conducted in neat (solvent-free) condition.

The present disclosure is intended to include a method of synthesizing the compound of formula (I) of the first aspect in which X is S by replacing the urea of formula (IV) in the aforementioned method with a thiourea of formula (V)

(V)

or a salt, solvate, tautomer or stereoisomer thereof, wherein (i) $R_3$ is selected from the group consisting of a hydrogen, an optionally substituted alkyl, an optionally substituted cycloalkyl, and an optionally substituted arylalkyl, and (ii) $R_4$ is selected from the group consisting of a hydrogen, an optionally substituted alkyl, an optionally substituted cycloalkyl, and an optionally substituted arylalkyl.

In a preferred embodiment, the reaction is performed at a concentration of the enaminone in the range of 1-1,000 mM, preferably 5-500 mM, preferably 10-400 mM, preferably 20-300 mM, preferably 40-200 mM. In a preferred embodiment, the reaction is performed at a concentration of the aldehyde in the range of 1-1,000 mM, preferably 5-500 mM, preferably 10-400 mM, preferably 20-300 mM, preferably 40-200 mM. In a preferred embodiment, the reaction is performed at a concentration of the urea in the range of 1-1,000 mM, preferably 5-500 mM, preferably 10-400 mM, preferably 20-300 mM, preferably 40-200 mM. In one or more embodiments, a molar ratio of the enaminone of formula (II) to the aldehyde of formula (III) is in the range of 1:3 to 3:1, preferably 1:2 to 2:1, preferably 2:3 to 3:2, or about 1:1. In one or more embodiments, a molar ratio of the aldehyde of formula (III) to the urea of formula (IV) is in the range of 1:3 to 3:1, preferably 1:2 to 2:1, preferably 2:3 to 3:2, or about 1:1.

In one or more embodiments, the acid is present at a concentration of 0.01-200 mM, preferably 0.1-100 mM, preferably 1-80 mM, preferably 5-60 mM, preferably 10-40 mM relative to a total volume of the mixture. Exemplary acids that may be suitable for the reaction described herein include, without limitation, acetic acid, fluoroacetic acid, chloroacetic acid, dichloroacetic acid, trifluoroacetic acid, trichloroacetic acid, propionic acid, formic acid, citric acid, citrate acid, oxalate acid, hydrochloric acid, sulfuric acid, phosphoric acid, sulfamic acid, fluoroboric acid, hexafluorophosphoric acid, benzoic acid. Preferably, acetic acid is employed. In certain embodiments, a Lewis acid may be used in addition to, or in lieu of acetic acid which include, but are not limited to, $BF_3$, $BCl_3$, $AlCl_3$, $AlBr_3$, $TiCl_4$, $Me_2AlCl$, $SnCl_4$, and $FeCl_3$.

Figure 3:
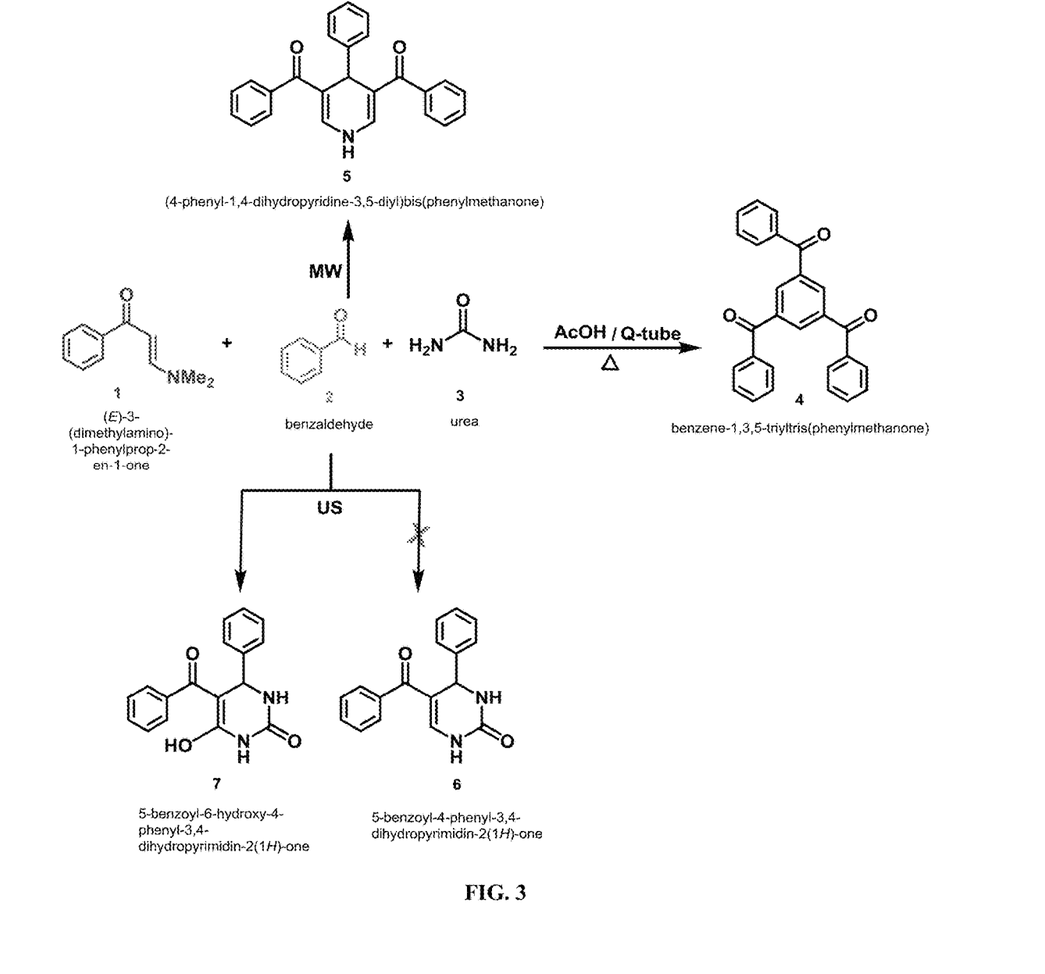
FIG. 3 illustrates different products 4, 5, and 7 formed by reacting enaminone 1, benzaldehyde 2, and urea 3 under different conditions.
Figure 4:
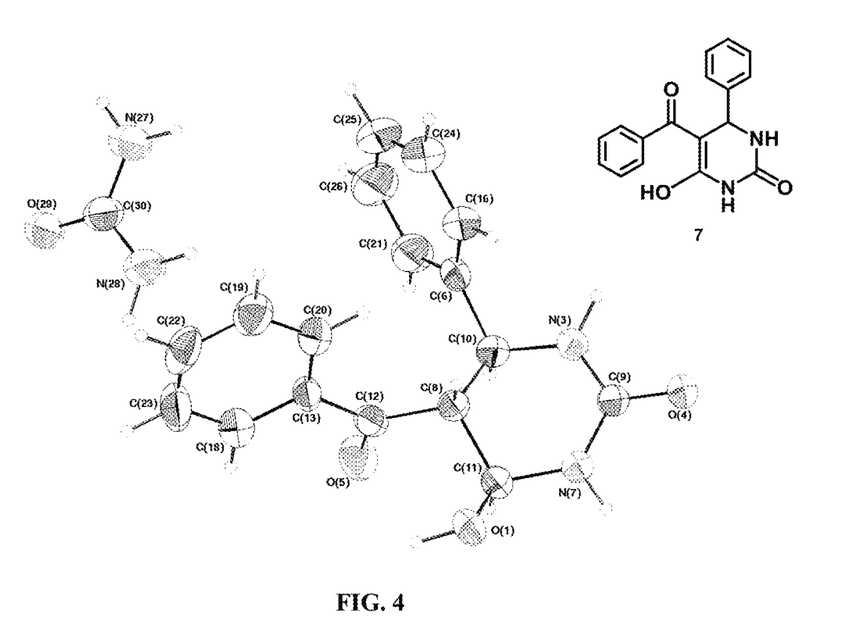
FIG. 4 is an Oak Ridge Thermal-Ellipsoid Plot Program (ORTEP) drawing of the crystal structure of compound 7 (or: 5-benzoyl-6-hydroxy-4-phenyl-3,4-dihydropyrimidin-2(1H)-one).

Previous studies have reported the employment of microwave irradiation in Biginelli reaction generated promising results [Behbehani, H; Ibrahim, M. H. Microwave-assisted synthesis in water: first one-pot synthesis of a novel class of polysubstituted benzo[4,5] imidazo[1,2-b] pyridazines via intramolecular SNAr. RSC Adv., 2015, 5, pp. 89226-89237, incorporated herein by reference in its entirety]. However, it was found in our recent experiments that only Hantzsch pyridines were produced as major products using this variation of the reaction. As shown in FIG. 3, a dihydropyridine 5 was obtained upon microwave (MW) irradiation of the enaminone 1, benzaldehyde 2, and urea 3. It is also of value to note that conventional heating of the above mentioned mixture has been claimed to afford Biginelli adduct 6 and its derivatives, although in our laboratories Hantzsch pyridines were isolated as reaction products. In addition, reacting the enaminone 1, with benzaldehyde 2 and urea 3 in dioxane in a Q-tube in the presence of AcOH and $NH_4OAc$ afforded compound 4 only. It was observed that applying pressure to the reaction mixture enhanced the rate of the dimerization reaction more than that of other potential reactions leading to formation of 5 or 6 (FIG. 3). However, when the reaction mixture of enaminone 1, benzaldehyde 2, and urea 3 was treated with ultrasound irradiation, a dihydropyrimidone 7 was the only product isolated (FIG. 3). It is believed that reactive OH radicals are generated under ultrasound irradiation. In addition, OH radicals are considered as a very strong oxidizer.

In one or more embodiments, the mixture is subjected to ultrasound irradiation for 0.1-12 hours, preferably 0.25-6 hours, preferably 0.5-3 hours, preferably 1-2 hours at a temperature of 30-150° C., preferably 40-120° C., preferably 50-90° C., preferably 60-80° C., or about 70° C. The ultrasonic irradiation may be carried out in an ultrasonic bath, with an ultrasonic probe, or using an ultrasonic processor having a frequency of 5-400 kHz, preferably 10-200 kHz, preferably 20-100 kHz, preferably 25-75 kHz, preferably 30-50 kHz. An external heat source, such as a water bath or an oil bath, an oven, microwave, or a heating mantle, may be employed to heat the mixture. In some embodiments, the mixture is heated with microwave irradiation. The mixture may be further agitated throughout the duration of the reaction by employing a rotary shaker, a magnetic stirrer, a centrifugal mixer, or an overhead stirrer. In another embodiment, the reaction mixture is left to stand (i.e. not stirred).

The compound of formula (I) may be isolated and purified by methods known to those skilled in the art, such as crystallization, filtration through a celite containing cartridge, evaporating the reaction mixture to dryness, aqueous work-up, extraction with organic solvents, distillation, column chromatography, and high pressure liquid chromatography (HPLC) on normal phase or reversed phase. Preferred methods include filtration and recrystallization. An isolated yield of the compound may be at least 40%, preferably at least 50%, preferably at least 60%, preferably at least 70%, preferably at least 80%, preferably at least 90%. As defined herein, a limiting reagent is determined as the starting reagent that is present in the smallest molar amount, including the enaminone of formula (II), the aldehyde of formula (III) and the urea of formula (IV). The isolated yield is calculated as (mole of the isolated compound/mole of the limiting reagent)×100%.

The examples below are intended to further illustrate protocols for preparing and characterizing the compounds of formula (I), and are not intended to limit the scope of the claims.

EXAMPLE 1

Discussion of Synthetic Methodology

A new compound, 5-benzoyl-6-hydroxy-4-phenyl-3,4-dihydropyrimidin-2(1H)-one, was synthesized by conducting a Biginelli reaction under ultrasound irradiation. By following a reaction between an enaminone 1, an aromatic aldehyde 2 and urea 3 in acetic acid, in the presence of ammonium acetate, we observed that product obtained was dependent on applied reaction conditions. As illustrated in FIG. 3, 1, 3, 5-triaroylbenzene was formed with 50% yield in a Q-tube under pressure only. On the other hand, ultrasound irradiation of the same mixture led to a different end product. Under ultrasonic irradiation, a new novel compound determined to be 5-benzoyl-6-hydroxy-4-phenyl-3,4-dihydropyrimidin-2(1H)-one was obtained instead. The chemical structure of this reaction product was firmly established using x-ray crystallography. In addition, a reaction mechanism to account for the formation of the observed product was proposed.

EXAMPLE 2

General Procedures for Ultrasound-Assisted Synthesis of 7

One drop of glacial acetic acid (AcOH) was added as a catalyst to a mixture of enaminone acetophenone 1 (0.01 mol), aromatic aldehyde 2 (0.01 mol), and urea 3 (0.01 mol) in the presence of ethanol (70 mL) as solvent in a Pyrex conical flask. Then, the mixture was heated under ultrasound irradiation (Ultrasound, micropreess controlled-2004, high intensity ultrasonic processor with a temperature controller, 750 W) at 70° C. for 1 hour. The ultrasonic frequency of the cleaning bath used equals 25 KHz. The reaction temperature was stabilized at around 70° C. by addition or removal of water in ultrasonic bath to keep the required temperature. Progress of the reaction was monitored by thin layer chromatography (TLC). At the end of the reaction, the mixture was left to cool to room temperature. The solid product was then observed and collected by filtration, dried, and recrystallized from ethanol to give pyrimidine derivative 7.

EXAMPLE 3

5-benzoyl-6-hydroxy-4-phenyl-3,4-dihydropyrimidin-2(1H)-one (Compound 7)

Light yellow crystals were collected in 74% yield,
m.p. 267° C.,
$R_f$=0.72 (5% MeOH in $CH_2Cl_2$),
IR: (KBr, $cm^{-1}$): 3330 (NH), 3050 (CH aromatic), 1700 (CO), and 1640 (CO),
$^1$H NMR (400 MHz, DMSO-$d_6$): δ=5.00 (s, 1H, CH), 7.19-7.94 (m, 10H, Ar—H), 8.28 (s, 1H, OH), 8.87 (brs, 1H, NH), 8.88 (brs, 1H, NH) ppm.

$^{13}$C NMR (100 MHz, DMSO-d$_6$): δ=55.86 (CH), 120.52 (C=C), 133.02 (CH), 127.05-139.51 (Ar—H), 155.01 (C=O), 199.59 (C=O) ppm.

MS: 294 (M$^+$), Anal. Calcd. For C$_{17}$H$_{14}$N$_2$O$_3$ (294.10): C, 69.38; H, 4.79; N, 9.52; O, 16.31.

The invention claimed is:

1. A compound of formula (I)

or a salt thereof, a solvate thereof, a tautomer thereof, a stereoisomer thereof, or a mixture thereof;
wherein:
each R$_1$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, and a halogen;
each R$_2$ is independently selected from the group consisting of a hydrogen, an optionally substituted alkyl, an optionally substituted cycloalkyl, an optionally substituted arylalkyl, an optionally substituted aryl, an optionally substituted alkoxy, a hydroxy, a halogen, a nitro, and a cyano;
R$_3$ is selected from the group consisting of a hydrogen, an optionally substituted alkyl, an optionally substituted cycloalkyl, and an optionally substituted arylalkyl;
R$_4$ is selected from the group consisting of a hydrogen, an optionally substituted alkyl, an optionally substituted cycloalkyl, and an optionally substituted arylalkyl; and
X is O or S.

2. The compound of formula (I) claim 1, wherein each R$_1$ is a hydrogen.

3. The compound of formula (I) of claim 1, wherein each R$_2$ is a hydrogen.

4. The compound of formula (I) of claim 1, wherein R$_3$ is a hydrogen.

5. The compound of formula (I) of claim 1, wherein R$_4$ is a hydrogen.

6. The compound of formula (I) of claim 1, wherein X is O.

7. The compound of formula (I) of claim 1, which is

8. A pharmaceutical composition, comprising:
the compound of formula (I) of claim 1; and
a pharmaceutically acceptable carrier and/or excipient.

9. The pharmaceutical composition of claim 8, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

10. The pharmaceutical composition of claim 8, which comprises up to 10% by weight of the pharmaceutically acceptable carrier and/or excipient relative to a total weight of the pharmaceutical composition.

11. The pharmaceutical composition of claim 8, wherein the compound is or a salt thereof, a solvate thereof, or a mixture thereof.

* * * * *